(12) United States Patent
Ikeda et al.

(10) Patent No.: US 11,186,818 B2
(45) Date of Patent: Nov. 30, 2021

(54) CULTURE MEDIUM AND METHOD FOR PRODUCING CULTURE MEDIUM

(71) Applicant: Panasonic Intellectual Property Management Co., Ltd., Osaka (JP)

(72) Inventors: Kouji Ikeda, Hyogo (JP); Taichi Nakamura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 675 days.

(21) Appl. No.: 15/901,993

(22) Filed: Feb. 22, 2018

(65) Prior Publication Data

US 2018/0245035 A1    Aug. 30, 2018

(30) Foreign Application Priority Data

Feb. 27, 2017  (JP) .............................. JP2017-035573
Feb. 27, 2017  (JP) .............................. JP2017-035574

(51) Int. Cl.
*C12M 1/32*    (2006.01)
*C12N 5/00*    (2006.01)
*C12M 1/00*    (2006.01)
*C12M 1/12*    (2006.01)

(52) U.S. Cl.
CPC ........... *C12N 5/0018* (2013.01); *C12M 23/12* (2013.01); *C12M 23/20* (2013.01); *C12M 25/14* (2013.01); *C12N 2539/00* (2013.01)

(58) Field of Classification Search
CPC ............................. C12M 23/12; C12M 25/14
See application file for complete search history.

(56) References Cited

U.S. PATENT DOCUMENTS

| 5,571,721 A | * | 11/1996 | Turner | .................. B01L 3/5085 |
| | | | | 359/398 |
| 2008/0194010 A1 | | 8/2008 | Liu | |
| 2014/0057346 A1 | * | 2/2014 | Johnson | ................. C12M 23/12 |
| | | | | 435/305.1 |
| 2018/0251714 A1 | | 9/2018 | Liu et al. | |

FOREIGN PATENT DOCUMENTS

| JP | 2010-517590 A | 5/2010 |
| JP | 2017-046676 A | 3/2017 |
| WO | 2016/060260 A1 | 4/2016 |

OTHER PUBLICATIONS

Japanese Office Action issued in Japanese Patent Application No. JP2017-035573 dated Feb. 5, 2019.

* cited by examiner

*Primary Examiner* — Jonathan M Hurst
(74) *Attorney, Agent, or Firm* — Pearne & Gordon LLP

(57) ABSTRACT

Provided is a culture medium including fibers aligned in one direction, and a method for producing the same. The culture medium includes: a substrate; a frame body that includes a first surface, a second surface opposite therefrom, and one or more through holes extending from the first surface through the second surface, and that is mounted to the substrate such that the first surface is opposed thereto; a plurality of aligned fibers interposed between the substrate and the first surface; and a bonding portion that bonds the substrate, the plurality of aligned fibers, and the frame body, wherein at least a part of the plurality of aligned fibers is exposed from a first opening that is formed in the first surface by the through hole.

7 Claims, 10 Drawing Sheets

CULTURE MEDIUM AND METHOD FOR PRODUCING CULTURE MEDIUM

CROSS REFERENCE TO RELATED APPLICATIONS

The present application is based on and claims priority under 35 U.S.C. § 119 with respect to the Japanese Patent Application Nos. 2017-035573 and 2017-035574 both filed on Feb. 27, 2017 of which entire contents are incorporated herein by reference into the present application.

TECHNICAL FIELD

The present invention relates to a culture medium and a method for producing a culture medium, and particularly relates to a culture medium including fibers aligned in one direction, and a method for producing the same.

BACKGROUND ART

In recent years, a fiber base material is gathering attention as a culture medium for culturing biological tissues and microorganisms (see Japanese Laid-Open Patent Publication (Translation of PCT Application) No. 2010-517590). The fiber base material is, for example, a woven fabric, a knitted fabric, or a non-woven fabric, and has a three-dimensional structure. Therefore, a biological tissue or a microorganism can be cultured in vitro in a state closely resembling a physiological environment.

When a biological tissue or a microorganism has a directionality in growth, it is desirable that the fibers constituting the fiber base material are aligned in a certain direction. The reason is that this facilitates the growth of the biological tissue or the microorganism. However, usually, the fiber base material is retained in shape by the entanglement between the fibers, and does not have such alignment performance as that described above.

SUMMARY OF INVENTION

An aspect of the present invention relates to a culture medium including: a substrate; a frame body that includes a first surface, a second surface opposite therefrom, and one or more through holes extending from the first surface through the second surface, and that is mounted to the substrate such that the first surface is opposed thereto; a plurality of aligned fibers interposed between the substrate and the first surface; and a bonding portion that bonds the substrate, the plurality of aligned fibers, and the frame body, wherein at least a part of the plurality of aligned fibers is exposed from a first opening that is formed in the first surface by the through hole.

Another aspect of the present invention relates to a method for producing a culture medium, the method including the steps of: preparing a frame body that includes a first surface, and a second surface opposite therefrom, and one or more through holes extending from the first surface through the second surface, and that includes a first bonding portion on the first surface; spinning a starting material liquid of fibers from a nozzle to generate the fibers, and depositing the fibers so as to circumvent a circumferential surface of a winding rotational body, to form a plurality of aligned fibers; transferring the plurality of aligned fibers onto the first surface of the frame body via the first bonding portion, while rotating the winding rotational body; and mounting the frame body having the plurality of aligned fibers transferred thereon to a substrate such that the first surface is opposed to the frame body.

DETAILED DESCRIPTION

[Culture Medium]

Figure 1:
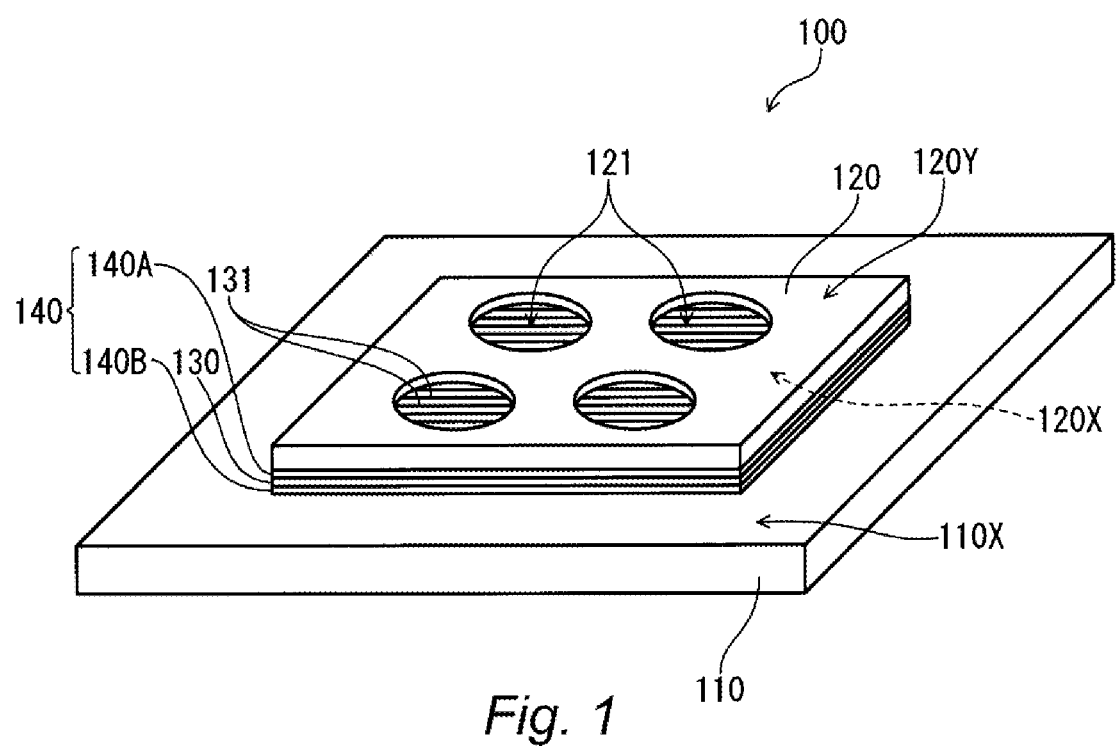
FIG. 1 is a perspective view schematically showing a culture medium according to the present invention.

A culture medium according to the present embodiment can be suitably used for a potential measurement device for measuring the potentials of a biological tissue and a microorganism in a state in which the biological tissue and the microorganism are held thereon. An example of the culture medium is shown in FIG. 1. FIG. 1 is a perspective view schematically showing a culture medium 100. The culture medium 100 includes a substrate 110, a frame body 120 mounted on the substrate 110, a plurality of aligned fibers 130 interposed between the substrate 110 and the frame body 120. Note, however, that the plurality of aligned fibers 130 is disposed not on the entire surface of a mounting surface 110X of the substrate 110 on which the frame body 120 is mounted, but is disposed within a region opposed to one principal surface (first surface 120X) of the frame body 120. Since the plurality of aligned fibers 130 is disposed only on the necessary portion, a high productivity can be achieved. The culture medium 100 may be housed in a holder or the like as needed, and be disposed in a potential measurement device.

(Plurality of Aligned Fibers)

A plurality of aligned fibers 130 (hereinafter referred to as a "group of fibers 130") is constituted by plural fibers 131. In the group of fibers 130, the fibers 131 are aligned in one direction. "Plural fibers 131 are aligned in one direction" means either that the fibers 131 do not intersect each other in the group of fibers 130, or that an average angle at which the fibers 131 intersect each other is above 0° and 60° or less. In this manner, when the fibers 131 are in the aligned state, the fibers 131 can be easily stretched along the alignment direction of the fibers 131, so that the stress applied to the biological tissue or the microorganism is reduced. This facilitates the growth of the biological tissue and the microorganism along the alignment direction of the fibers 131.

Figure 11:
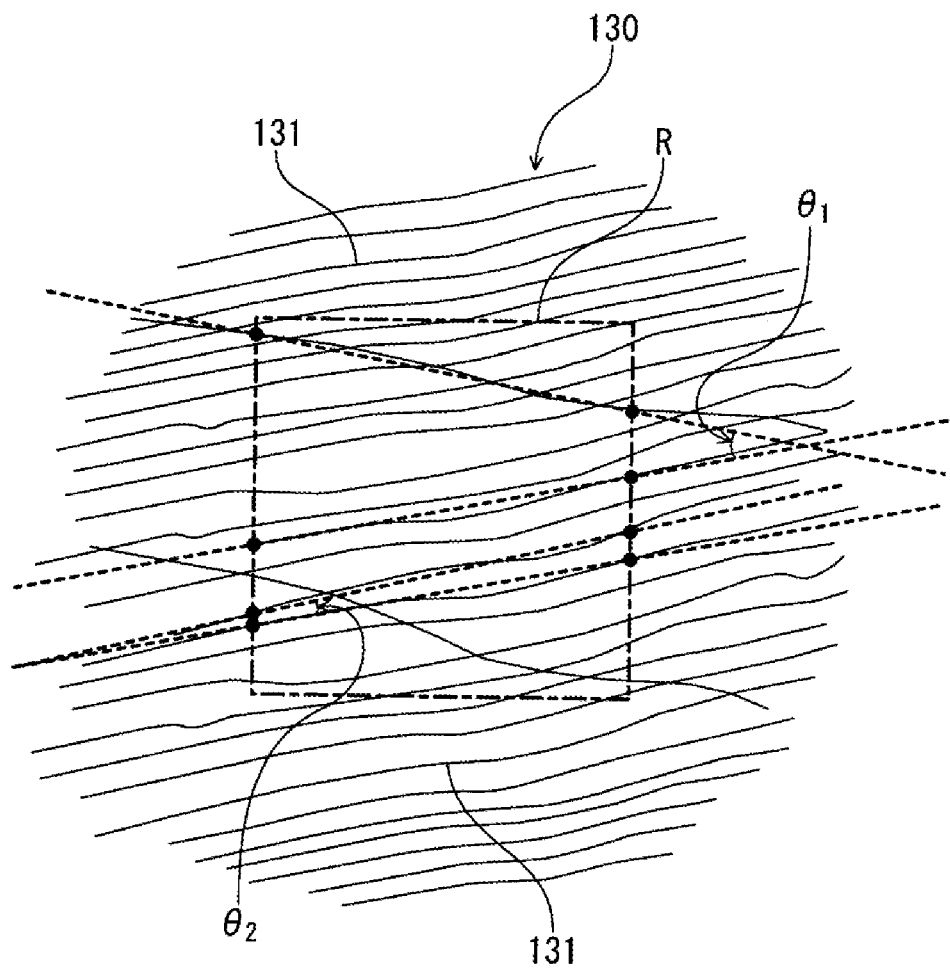
FIG. 11 is a plan view schematically showing a partial region of a plurality of aligned fibers for illustrating an alignment of fibers.

Here, an average angle at which the fibers 131 intersect each other can be determined by intersections between the fibers 131 in the average lengthwise direction. The average lengthwise direction of the fibers 131 can be determined based on, for example, a SEM image of the group of fibers 130 as viewed from the direction of the normal thereof. FIG. 11 is a schematic plan view of the group of fibers for illustrating the alignment of fibers. FIG. 11 simulates a state of the group of fibers 130 in a SEM image obtained by capturing an image of the group of fibers 130 from the direction of the normal. With the group of fibers 130 composed of the fibers 131 being viewed from the direction of the normal, a square region R having a predetermined size (for example, 100 μm×100 μm) is set. At this time, the region R is determined such that 12 or more fibers 131 can fit within the region R, and that 50% or more of the fibers 131 located within the region R intersect two opposed sides of the region R. For a given fiber 131, the direction of a straight line (dotted line in FIG. 11) connecting two points intersecting the above-described two opposed sides in the region R is determined to be an average lengthwise direction of the fiber 131.

An average angle at which the fibers 131 intersect each other is determined, for example, by further arbitrarily selecting two fibers 131 from the plural (for example, 20) fibers 131 arbitrarily selected in the above-described region R, and determining the angle (for example, $\theta_1$ in FIG. 11) at which average lengthwise directions of the fibers 131 intersect. Then, different two fibers 131 are selected, and the angle (for example, $\theta_2$ in FIG. 11) at which the average lengthwise directions of the fibers 131 intersect is determined. Such an operation is performed for the rest of the selected fibers 131 (for example, 16 fibers). Then, an average of the angles is calculated, and the calculated angle is determined as an average angle at which the fibers 131 intersect each other.

The area ratio of the fibers 131 per unit area of the group of fibers 130 can be selected from 10 to 90%. For example, for use in the culturing of myocardial cells or a potential measurement device, it is preferable that the group of fibers 130 is very thin, the ratio of the fibers 131 per unit is 20 to 50%, preferably 30 to 40%, and the fibers 131 are deposited 131 so as to be uniformly dispersed. Note that the area ratio of the fibers 131 can be determined as follows. For a region having a predetermined area (for example, an elliptical region having a minor axis of 3 mm and a major axis of 6 mm) of the group of fibers 130 on one principal surface (for example, the upper surface) of the group of fibers 130, an image is obtained with an optical microscope or the like. Binarization processing is performed on the obtained image to calculate an area occupied by the fibers 131, and the area is converted into an area ratio (%) per unit area.

The material of the fibers 131 is not particularly limited so long as it can be used as a culture medium for biological tissues and microorganisms. In particular, it is preferable that the fibers 131 include a block polymer including a polystyrene block and a polybutadiene block, and a styrene resin different from the block polymer because these materials have high affinity for biological tissues and microorganisms, and are less likely to apply stress to biological tissues and microorganisms during culturing. The fibers 131 may include various additives as needed.

The block polymer may be, for example, a diblock polymer in which a polybutadiene (PB) block and a polystyrene (PS) block are connected, but is preferably a polyblock polymer that is a triblock or higher block polymer in which PB blocks and PS blocks are alternately connected. From the viewpoint of ensuring the affinity for the styrene resin, the block polymer preferably includes a PS block at least at its terminal end. The PB block enhances the flexibility and ductility of the resulting fibers 131.

The PB block content in the block polymer is, for example, 10 to 30 mass %, preferably 15 to 30 mass %, more preferably 20 to 30 mass % or 20 to 25 mass %. When the PB block content is within such a range, the affinity for the styrene resin is increased, facilitating generation of homogeneous fibers 131. Additionally, the resulting fibers 131 have high flexibility and high ductility. Furthermore, high spinnability can be ensured in the case of generating the fibers 131 by electrospinning.

As the styrene resin, a polymer different from the above-described block polymers is used. Examples of the styrene resin include polystyrenes (styrene homopolymers), and copolymers of styrenes with other copolymerizable monomers. The styrene resin may be used alone or in a combination of two or more.

From the viewpoint of achieving both the flexibility and the ease of formation of the fibers 131, the mass ratio (=block polymer:styrene resin) of the block polymer and the styrene resin is, for example, 2:1 to 1:5, preferably 1:1 to 1:4. In particular, in the case of forming the group of fibers 130 by electrospinning using a solution, the aforementioned mass ratio range can facilitate dissolution of the block polymer and the styrene resin in a solvent, thus making it also possible to ensure high spinnability.

The average fiber diameter of the fibers 131 is, for example, preferably 0.5 to 10 μm, more preferably 1 to 5 μm, particularly preferably 1.5 to 4 μm. Note that the average fiber diameter is an average value of the diameters of the fibers 131. The diameter of the fibers 131 is a diameter of a cross-section perpendicular to the lengthwise direction of the fibers 131. When such a cross-section is not circular, the largest diameter may be considered as a diameter. The width of a fiber 131 in a direction perpendicular to the lengthwise direction thereof as viewed from a direction of the normal of one principal surface of the group of fibers 130 may be considered as the diameter of the fiber. The average fiber diameter is, for example, an average value of the diameters at arbitrary locations of arbitrary 10 fibers included in the group of fibers 130.

(Frame Body)

The frame body 120 includes a first surface 120X, a second surface 120Y opposite therefrom, and one or more through holes 121 extending from the first surface 120X through the second surface 120Y. The group of fibers 130 is disposed on the first surface 120X so as to cover at least a part of the through holes 121. That is, the group of fibers 130

(fibers 131) is exposed from openings (first openings 121*a*, see FIG. 2A etc.) of the through holes 121 on the first surface 120X side.

When the frame body 120 has been mounted on the substrate 110, the first openings 121*a* are closed by the substrate 110 via the group of fibers 130, to form at least one depression on the mounting surface 110X of the substrate 110. A nutrient solution containing a biological tissue or a microorganism is injected into this depression from openings (second openings) of the through holes 121 on the second surface 120Y side. The injected biological tissue or microorganism grows with the group of fibers 130 as a scaffold. Since the fibers 131 constituting the group of fibers 130 are aligned along one direction, the biological tissue or the microorganism can grow in a low stress state along the lengthwise direction of the fibers 131.

The material of the frame body 120 is not particularly limited, and may be a glass or a resin (including an elastomer). The size of the frame body 120 is not particularly limited so long as the entire surface of the first surface 120X can be opposed to the substrate 110 and the wiring of electrodes (see the following description) disposed on the substrate 110 is not obstructed.

The number of the through holes 121 is also not particularly limited, and may be appropriately set according to the size and the usage of the frame body 120. The shapes and the sizes of the first opening 121*a* and the second opening are also not particularly limited, and may be appropriately set according to the usage and the like. The shapes and the sizes of the first opening 121*a* and the second opening may be the same, or may be different. The shape of the above-described depression formed by the through hole 121 is not particularly limited. For example, when the first opening 121*a* and the second opening are both circular, the shape of the depression may be columnar, or may be conical. In particular, the above-described depression preferably has a conical shape that defines a large second opening, since the nutrient solution can be easily injected.

(Substrate)

The substrate 110 is insulating, and includes, for example, plural electrodes (first electrodes), which are not shown, and plural microelectrodes (second electrodes) electrically connecting to the first electrodes. The first electrodes are insulated from each other. The second electrodes are formed at a predetermined interval in a matrix form, and are insulated from each other.

The first electrodes are disposed so as not to be in contact with the group of fibers 130, whereas the second electrodes are disposed so as to be in contact with at least a part of the group of fibers 130. By measuring the voltage across the first electrode and the second electrode, it is possible to measure the potential of the group of fibers 130 (i.e., the biological tissue or the microorganism). In this manner, by measuring a potential change over time of the group of fibers 130 or a potential change thereof at the time of changing the conditions, it is possible to evaluate the state and the function of the biological tissue or microorganism based on this potential change. At this time, the biological tissue or microorganism is in a low stress state, so that it is possible to perform highly accurate evaluation. Furthermore, by applying a voltage across the first electrode and the second electrode, a stimulus (electric signal) can be applied to the biological tissue or microorganism, thus facilitating the growth thereof.

The substrate 110 is not particularly limited so long as it is insulating, and may be appropriately selected according to the usage. Examples of the substrate includes a glass plate, a quartz plate, and an acrylic plate. The first electrode is also not particularly limited, and may be appropriately selected according to the usage. Examples of the first electrode include an ITO (indium tin oxide) electrode and a platinum electrode.

The second electrode may be any electrode capable of measuring the potential of biological tissues and microorganisms, and can be appropriately selected according to the usage. The size of the second electrode, the distance between adjacent second electrodes, and the number of the second electrodes can be appropriately selected according to the type of the biological tissue or the microorganism and the size of samples thereof. The length of one side (the diameter in the case of a disk-shaped electrode) of the second electrode is, for example, 10 to 100 µm, or may be 15 to 60 µm. The distance between adjacent second electrodes (the distance between the centers of the second electrodes) is, for example, 50 to 1000 µm, or may be 50 to 500 µm.

(Bonding Portion)

The substrate 110, the frame body 120, and the group of fibers 130 are bonded via a bonding portion 140. The group of fibers 130 is an aggregate of the fibers 131 aligned in one direction. Accordingly, for example, when an adhesive is applied to the frame body 120, the adhesive enters between the fibers 131 and permeates to the substrate 110 side, to form a bonding portion 140 that bonds the frame body 120 and the substrate 110. Similarly, when an adhesive is applied to the substrate 110, the adhesive permeates to the frame body 120 side, to form a bonding portion 140 that bonds the frame body 120 and the substrate 110. In either case, a part of the group of fibers 130 is held so as to be embedded into the bonding portion 140. Note that no bonding portion 140 is formed in a region corresponding to the first opening 121*a*.

The material (adhesive) of the bonding portion 140 is not particularly limited, and examples thereof include a pressure-sensitive adhesive, a hot-melt adhesive, and a curable adhesive. The pressure-sensitive adhesive is applied to the substrate 110 or the frame body 120, and bonds the frame body 120, the group of fibers 130, and the substrate 110 by its viscosity. The material of the pressure-sensitive adhesive is not particularly limited, and examples thereof include a silicone resin. Examples of the silicone resin include dimethyl silicone and methylphenyl silicone.

The hot-melt adhesive is applied to the substrate 110 or the frame body 120 while being heated, and is cooled, thereby to bond the frame body 120, the group of fibers 130, and the substrate 110. The material of the hot-melt adhesive is not particularly limited, and, for example, contains, as a primary component (component that accounts for 50 mass % or more), a thermoplastic resin, including, for example, polyurethane, polyesters such as polyethylene terephthalate, copolymerized polyester such as a urethane-modified copolymerized polyester, polyamides, and polyolefins (for example, polypropylene and polyethylene).

The curable adhesive is applied to the substrate 110 or the frame body 120, and is cured by being irradiated with ultraviolet radiation or being heated, thereby to bond the frame body 120, the group of fibers 130, and the substrate 110. The type of the curable adhesive is not particularly limited, and examples thereof include a thermosetting resin and an ultraviolet curable resin. Examples of these resins include an acrylic resin and an epoxy resin. In the case of using the curable adhesive, it is preferable that the curable adhesive is brought into a semi-cured state before a transfer step, which will be described later. In this case, a curing operation is further performed before the transfer step, or after a mounting step, to completely cure the curable adhesive.

In particular, as the adhesive, a pressure-sensitive adhesive and a hot-melt adhesive are preferable in that a special curing step can be omitted, and a pressure-sensitive adhesive is further preferable in that a heating device for melting the adhesive is not necessary. Note that when the adhesive contains a hot-melt adhesive and/or a curable adhesive, the two members being "bonded via the bonding portion 140" means that these members are "bonded via a cured product of the adhesive".

The bonding portion 140 may be formed so as to be opposed to the entire surface of the first surface 120X except for the first opening, or may be partially formed at a position opposed to the first surface 120X. At this time, the adhesive may be applied to the frame body 120, or may be applied to the substrate 110. In particular, it is preferable that the adhesive is applied to the entire surface of the first surface 120X of the frame body 120 except for the first openings because the detachment of the first surface 120X from the group of fibers 130 can be suppressed. Furthermore, in this case, the distance between the group of fibers 130 and the substrate 110 (mounting surface 110X) tends to be smaller than the distance between the group of fibers 130 and the frame body 120 (first surface 120X) in the culture medium 100. Accordingly, the accuracy of measuring the potential of the group of fibers 130 is enhanced.

On the other hand, considering the detachment suppression for the group of fibers 130 and the adhesion between the substrate 110 and the frame body 120, it is preferable that the adhesive is applied to each of the first surface 120X of the frame body 120 and the mounting surface 110X of the substrate 110. A bonding portion (first bonding portion 140A) formed by the adhesive applied to the first surface 120X and a bonding portion (second bonding portion 140B) formed by the adhesive applied to the mounting surface 110X may be in contact with each other while they each contain the fibers 131 therein. For the sake of convenience, in the example shown in the drawings, the bonding portion 140 is shown as being separated into the first bonding portion 140A on the frame body 120 side and the second bonding portion 140B on the substrate 110 side across the group of fibers 130. In terms of adhesion, it is preferable that the first bonding portion 140A and the second bonding portion 140B contain an adhesive made of the same material (preferably, a pressure-sensitive adhesive). The first bonding portion 140A and the second bonding portion 140B may be opposed to each other on the entire surfaces thereof or may be partially opposed to each other.

The mass per unit area of the bonding portion 140 (or a total mass of the first bonding portion 140A and the second bonding portion 140B) is not particularly limited. In particular, from the viewpoint of ensuring the adhesion between the group of fibers 130 and the frame body 120, and also adhesion between the substrate 110 and the frame body 120, the above-described mass is preferably 0.5 to 100 mg/cm$^2$.

(Frame Body Fixing Portion)

The bonding portion 140 containing a pressure-sensitive adhesive is easily deformed by an external pressure, but is difficult to be brought back into the original state after being released from the external pressure. Therefore, for example, when an external pressure in the direction of the principal surface (for example, the first surface 120X) is applied to the frame body 120, the frame body 120 may be shifted in the direction of the first surface 120X relative to the substrate 110. When the frame body 120 is shifted relative to the substrate 110, the bonding portion 140 is deformed so as to follow the frame body 120. Since the group of fibers 130 is held by being partially embedded into the bonding portion 140, the deformation of the bonding portion 140 results in a disorder in the orientation of the fibers 131. In addition, a part of the deformed bonding portion 140 may be exposed from the first opening 121a. The bonding portion 140 exposed from the first opening 121a may disturb culturing, or cause a reduction in accuracy of the potential measurement. When an external pressure in a direction perpendicular to the first surface 120X is applied to the frame body 120, the bonding portion 140 may be deformed so as to be spread out, resulting in a change in the distance between the substrate 110 and the frame body 120. Since the group of fibers 130 is held by the bonding portion 140 as described above, such a deformation of the bonding portion 140 loosen the fibers 131.

It is preferable that a frame body fixing portion that fixes the frame body 120 to the substrate 110 is disposed on an outer edge on the first surface 120X of the frame body 120 in that the above-described deformation of the bonding portion 140 is suppressed. As the result of the above-described deformation of the bonding portion 140 being suppressed, the initial tension and alignment of the fibers 131 are maintained, thus improving the effect of promoting the growth of the biological tissue or microorganism.

Figure 2A:
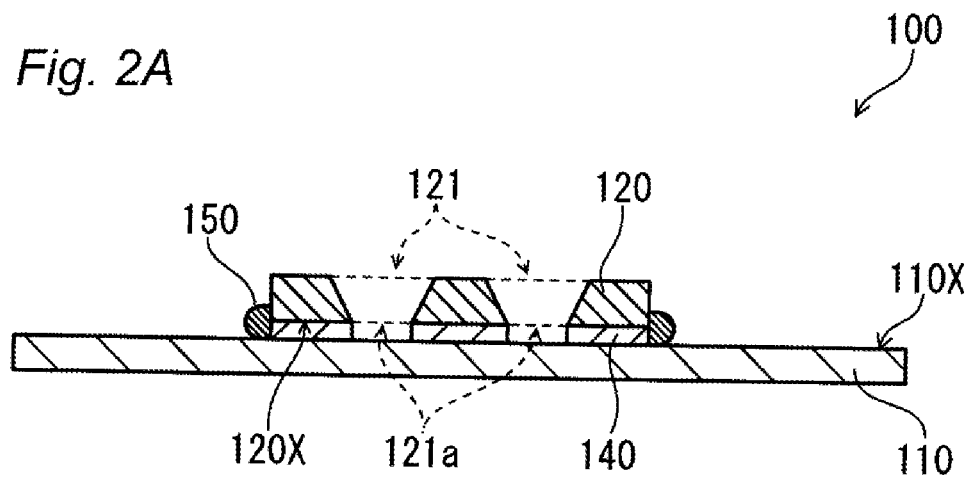
FIG. 2A is a cross-sectional view schematically showing a culture medium including a frame body fixing portion according to the present invention.
Figure 2B:
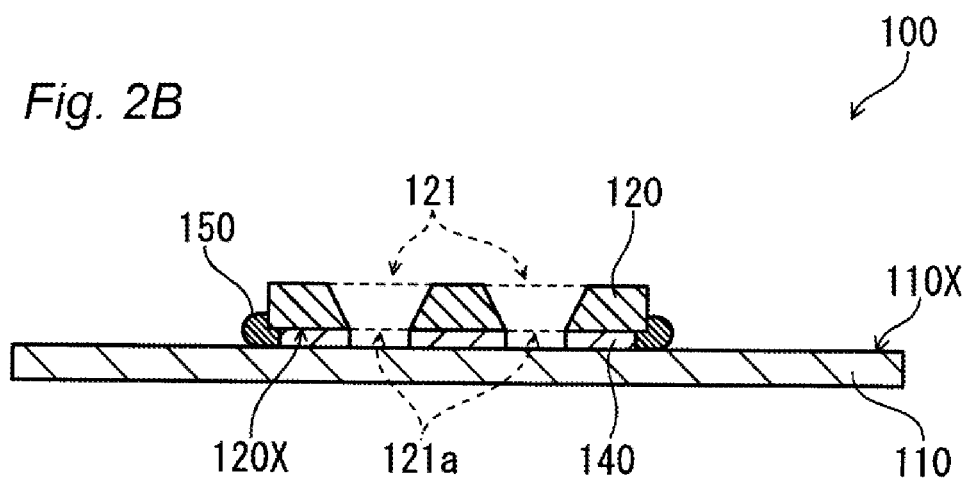
FIG. 2B is a cross-sectional view schematically showing another culture medium including a frame body fixing portion according to the present invention.
Figure 2C:
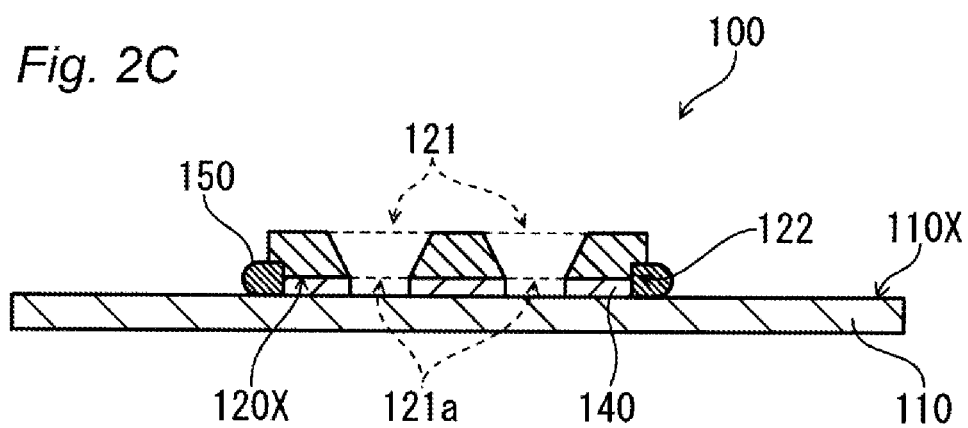
FIG. 2C is a cross-sectional view schematically showing still another culture medium including a frame body fixing portion according to the present invention.

The frame body fixing portion suppresses the deformation of the bonding portion 140 caused by an external pressure, for example, by being interposed between the frame body 120 and the substrate 110, to maintain the positional relationship between the substrate 110 and the frame body 120. In the following, the frame body fixing portion will be described with reference to FIGS. 2A to 2C. FIGS. 2A to 2C are cross-sectional views schematically showing the culture medium 100. Note, however, that illustration of the group of fibers 130 is omitted for the sake of convenience.

The frame body fixing portion 150 is disposed at at least a part of the outer edge on the first surface 120X of the frame body 120. The outer edge on the first surface 120X refers to a region including an outer peripheral portion of the first surface 120X and an end face of the frame body 120 on the first surface 120X side. For example, as shown in FIG. 2A, the frame body fixing portion 150 may be disposed so as to be in contact with the end face of the frame body 120 on the first surface 120X side and the mounting surface 110X. Note that in FIG. 2A, the bonding portion 140 containing a pressure-sensitive adhesive is formed on the entire surface of the first surface 120X except for the first openings 121a.

As shown in FIG. 2B, the bonding portion 140 may be formed on the first surface 120X at portions excluding the outer peripheral portion and the first openings 121a. In this case, the frame body fixing portion 150 may be disposed so as to be in contact with the end face of the frame body 120 on the first surface 120X, the mounting surface 110X, and the outer peripheral portion of the first surface 120X. This increases the contact area between the frame body fixing portion 150 and the frame body 120, thus enhancing the fixation of the frame body 120.

As shown in FIG. 2C, a notch 122 may be provided on the end face of the frame body 120 on the first surface 120X side. In this case, the frame body fixing portion 150 may be disposed so as to be in contact with the notch 122 and the mounting surface 110X. This can increase the volume of the frame body fixing portion 150, in addition to increasing the contact area between the frame body fixing portion 150 and the frame body 120, thus further enhancing the fixation of the frame body 120.

The frame body fixing portion 150 may be formed of a material that cannot be easily deformed by an external pressure. Examples of such a material include curable resins that are similar to the thermosetting resins and the ultraviolet curable resins described as the examples of curable adhesive. In this case, for example, after the frame body 120 is mounted on the substrate 110, the curable resin is applied to the perimeter of the frame body 120, and is heated, or irradiated with ultraviolet radiation. In the case of placing the frame body fixing portion 150 as shown in FIG. 2B or 2C, the curable resin may be applied to the first surface 120X before the frame body 120 is mounted onto the substrate 110, and then the frame body 120 may be mounted on the substrate 110, followed by heating or irradiation with ultraviolet radiation. The amount of application of the curable resin is not particularly limited, but is preferably 10 to 300 mg/cm$^2$, in view of the fixation of the frame body.

(Relief Portion)

A relief portion that absorbs deformation of the bonding portion 140 caused by an external pressure may be provided in place of the frame body fixing portion 150. In this case, contrary to the case of the frame body fixing portion 150, the positional relationship between the substrate 110 and the frame body 120 is maintained as the result of the deformation of the bonding portion 140 being suppressed.

Figure 3A:
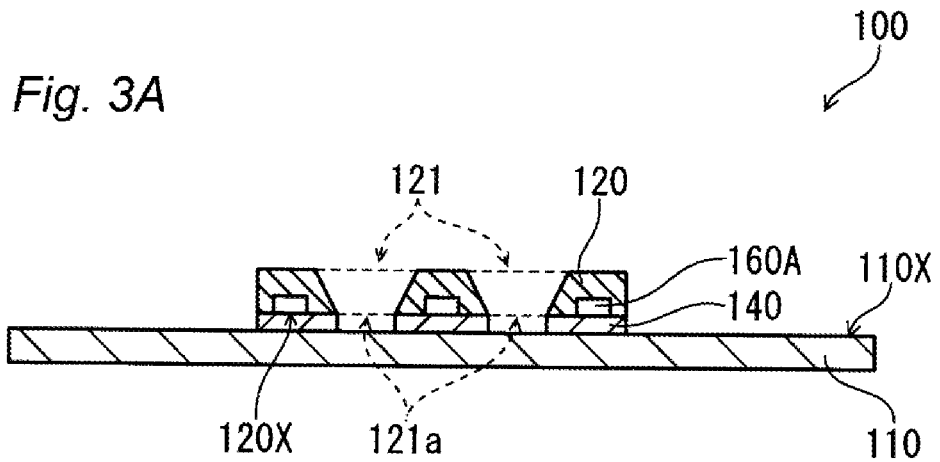
FIG. 3A is a cross-sectional view schematically showing a culture medium including a relief portion.
Figure 3B:
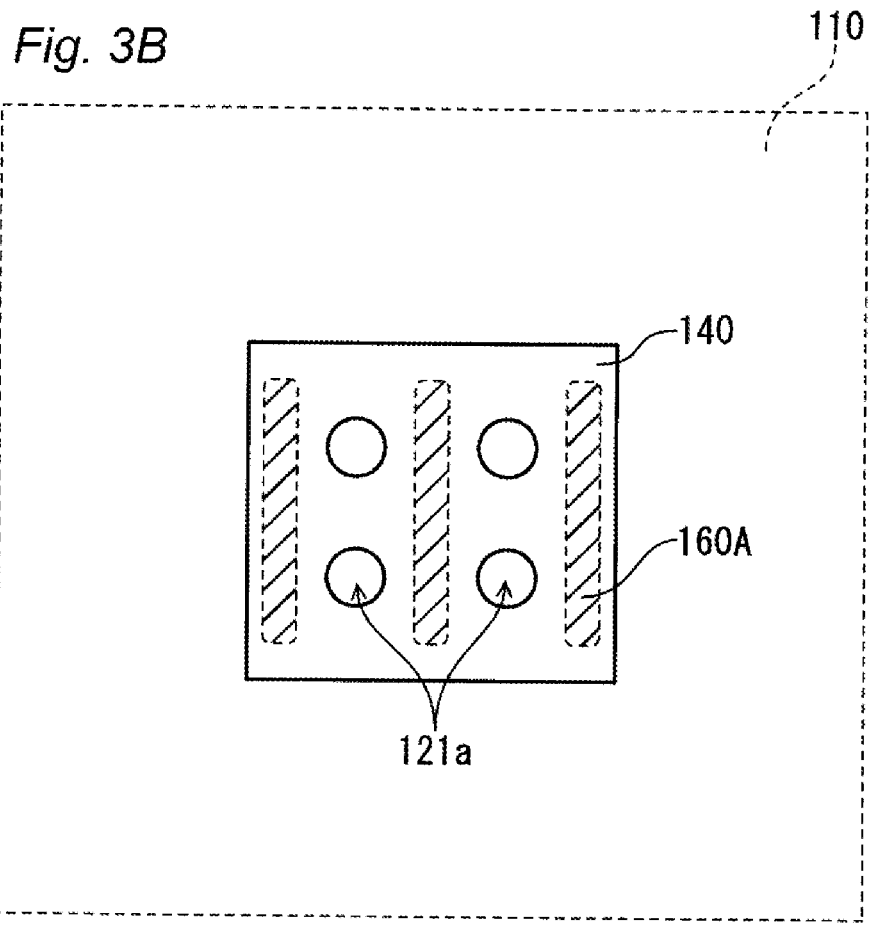
FIG. 3B is a plan view of the culture medium as viewed from the substrate side through the substrate.
Figure 4:
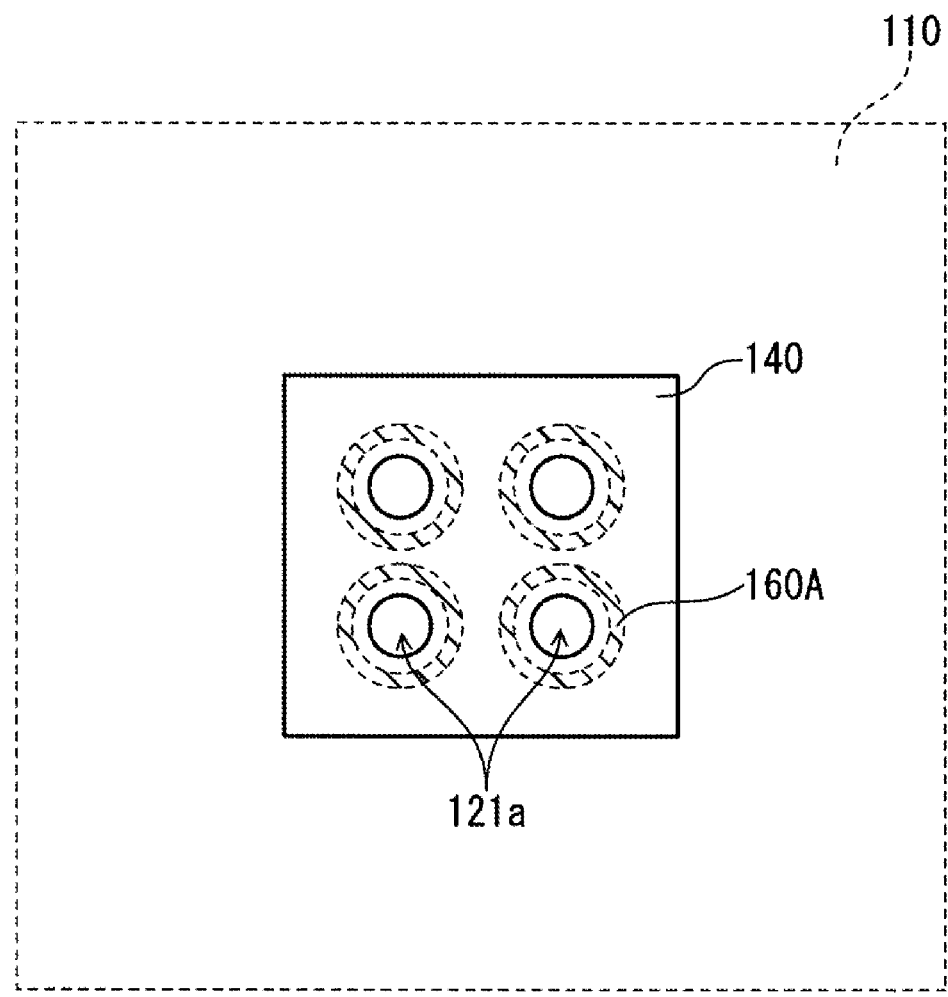
FIG. 4 is a plan view of another culture medium including the relief portion as viewed from the substrate side through the substrate.

In the following, a first embodiment of the relief portion will be described with reference to FIGS. 3A, 3B and 4. Here, illustration of the group of fibers 130 is also omitted for the sake of convenience. FIG. 3A is a cross-sectional view schematically showing a culture medium 100 including a relief portion 160A. FIG. 3B is a plan view of the culture medium 100 shown in FIG. 3A, when viewed through the substrate 110 from the substrate 110 side. FIG. 4 is a plan view of another culture medium 100 including the relief portion 160A, when viewed through the substrate 110 form the substrate 110 side. Note that in FIGS. 3B and 4, the relief portion 160A is hatched for the sake of convenience.

The relief portion 160A is a recess formed at a portion of the first surface 120X that correspond to a part of the bonding portion 140. When the bonding portion 140 is deformed by an external pressure, at least a part of the bonding portion 140 may be housed in the relief portion 160A. That is, at least a part of the amount of deformation of the bonding portion 140 is absorbed by the relief portion 160A. Accordingly, the positional relationship between the substrate 110 and the frame body 120 is maintained.

The size of the relief portion 160A is not particularly limited, and may be appropriately set according to the thickness and the like of the bonding portion 140. In particular, since the deformation of the bonding portion 140 can be easily suppressed while ensuring the adhesion, the area ratio (a total area ratio when plural relief portions 160A are provided) of the relief portion 160A to the area of the first surface 120X, as viewed from the direction of the normal of the first surface 120X, is preferably 5 to 20%. Since the deformation of the bonding portion 140 can be easily suppressed, the volume ratio (a total volume ratio when plural relief portions 160A are provided) of the relief portion 160A to the volume of the bonding portion 140 is preferably 20 to 80%.

The shape (arrangement) of the relief portion 160A is also not particularly limited. For example, the relief portion 160A may be linear as shown in FIG. 3B. In this case, it is preferable that the longitudinal direction of the relief portion 160A intersects the orientation direction of the fibers 131. This suppresses the deformation of the pressure-sensitive adhesive in the orientation direction of the fibers 131, thus further suppressing a disorder in the orientation of the fibers 131. At this time, linear relief portions 160A may be additionally disposed also in a direction intersecting the orientation direction of the fibers 131 so as to form a grid pattern.

As shown in FIG. 4, the relief portion 160A may have an annular shape that surrounds the first opening 121a. From the viewpoint of suppressing the extrusion of the pressure-sensitive adhesive from the first opening 121a, it is preferable that the relief portion 160A is disposed so as to be spaced apart from the first opening 121a. The distance (for example, an average distance at arbitrary 10 locations) between the relief portion 160A and the first opening 121a is not particularly limited, but may be 50 μm or more, for example.

Figure 5A:
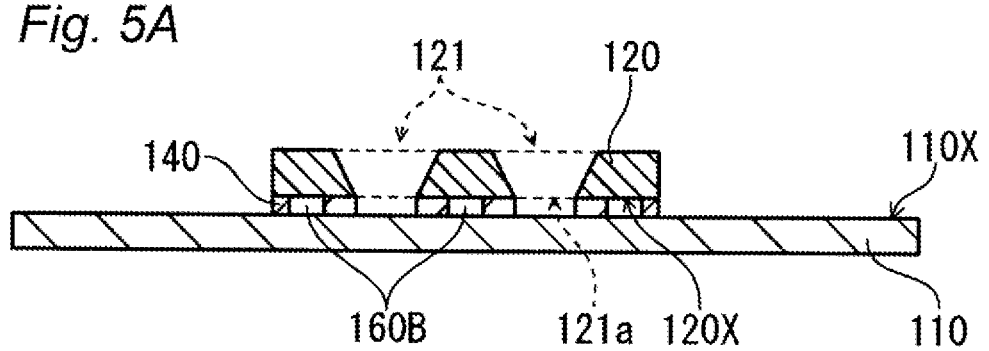
FIG. 5A is a cross-sectional view schematically showing a culture medium including another relief portion.
Figure 5B:
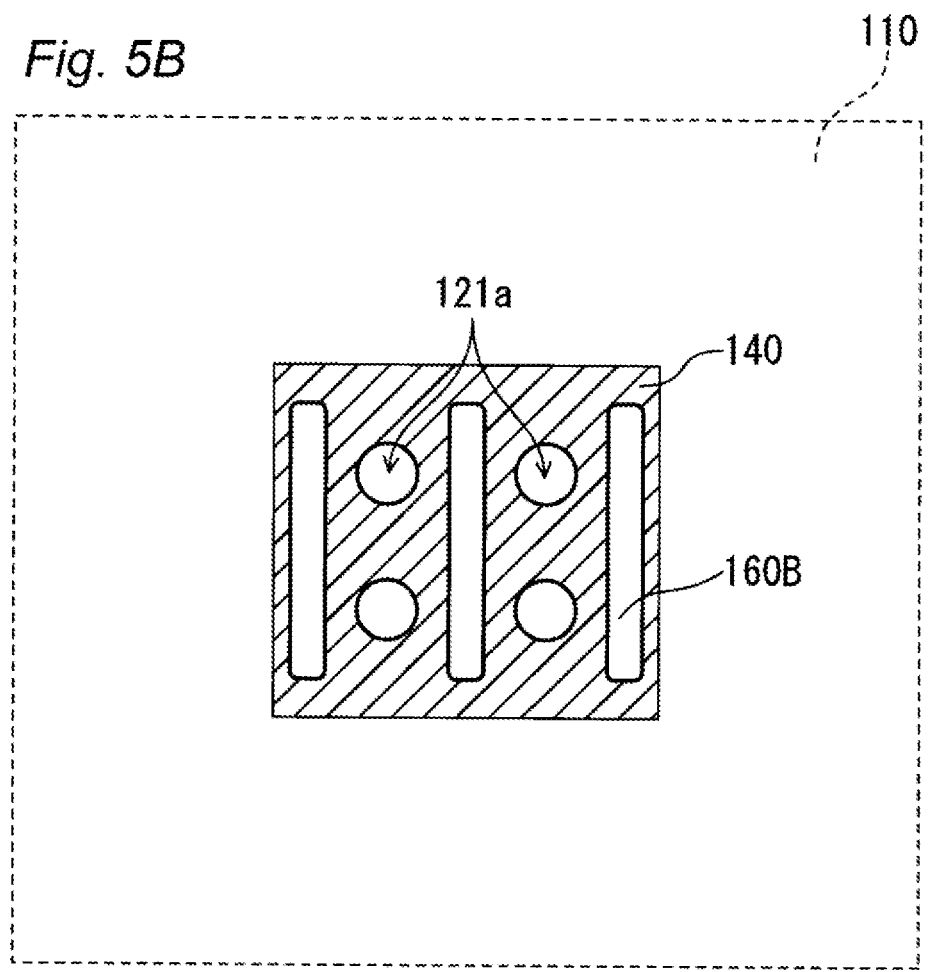
FIG. 5B is a plan view of the culture medium as viewed from the substrate side through the substrate.
Figure 6:
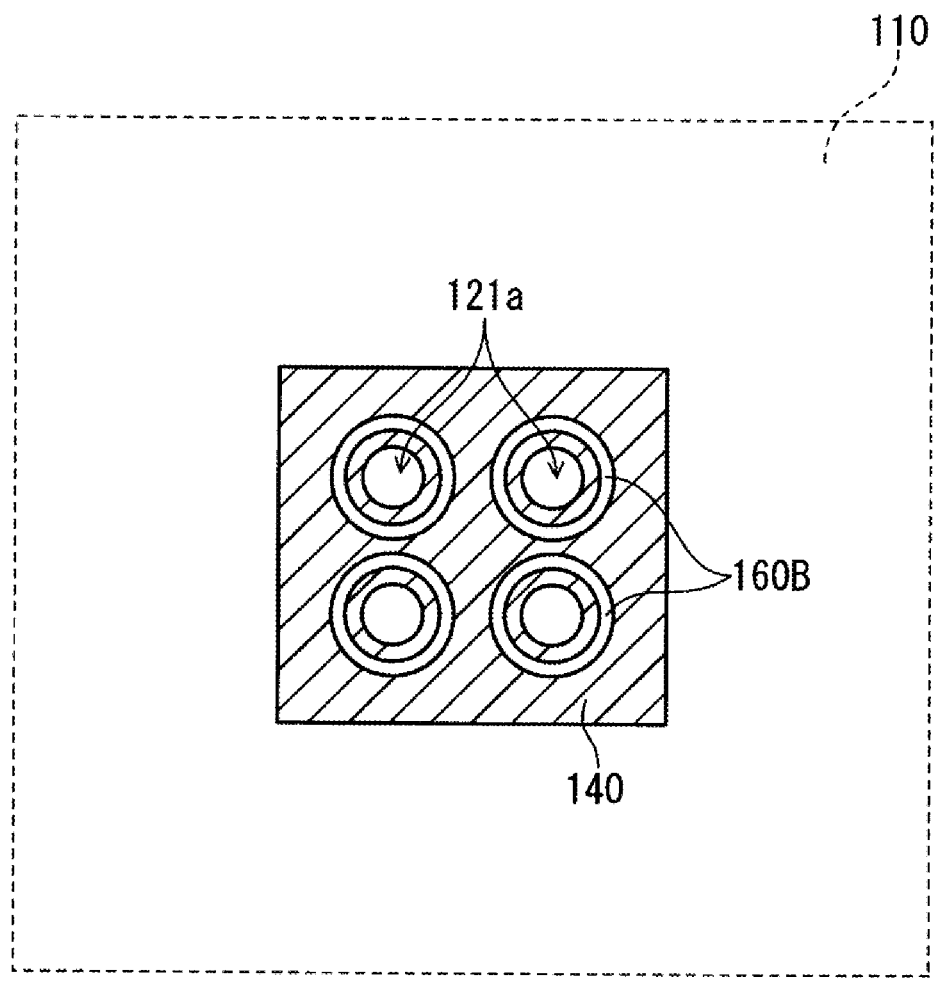
FIG. 6 is a plan view of another culture medium including the relief portion as viewed from the substrate side through the substrate.

A second embodiment of the relief portion will be described with reference to FIGS. 5A, 5B and FIG. 6. Here, illustration of the group of fibers 130 is also omitted for the sake of convenience. FIG. 5A is a cross-sectional view schematically showing a culture medium 100 including a relief portion 160B. FIG. 5B is a plan view of the culture medium 100 shown in FIG. 5A, when viewed through the substrate 110 from the substrate 110 side. FIG. 6 is a plan view of another culture medium 100 including the relief portion 160B, when viewed through the substrate 110 from the substrate 110 side. Note that in FIGS. 5B and 6, the bonding portion 140 is hatched for the sake of convenience.

The relief portion 160B is a space formed between the substrate 110 and the frame body 120. The relief portion 160B is formed, for example, by the bonding portion 140 being disposed at a part of the first surface 120X other than the first opening 121a. When an external pressure is applied to the bonding portion 140, the bonding portion 140 can be deformed by being moved into the relief portion 160B. That is, at least a part of the amount of deformation of the bonding portion 140 caused by the external pressure is absorbed by the relief portion 160B. Accordingly, the positional relationship between the substrate 110 and the frame body 120 is maintained.

The size of the relief portion 160B is not particularly limited, and may be appropriately set according to the thickness and the like of the bonding portion 140. In particular, since the deformation of the bonding portion 140 can be easily suppressed while ensuring the adhesion, the area ratio (a total area ratio when plural relief portions 160B are provided) of the relief portion 160B to the area of the bonding portion 140, as viewed from the direction of the normal of the first surface 120X is preferably 5 to 20%.

The shape (arrangement) of the relief portion 160B is also not particularly limited. For example, the relief portion 160B may be linear as shown in FIG. 5B. In this case, the longitudinal direction of the relief portion 160B intersects the orientation direction of the fibers 131. This suppresses the deformation of the pressure-sensitive adhesive in the orientation direction of the fibers 131, thus further suppressing a disorder in the orientation of the fibers 131. At this time, linear relief portions 160B may be additionally disposed also in a direction intersecting the orientation direction of the fibers 131 so as to form a grid pattern.

As shown in FIG. 6, the relief portion 160B may have an annular shape that surrounds the first opening 121a. From the viewpoint of suppressing the extrusion of the pressure-sensitive adhesive from the first opening 121a, it is preferable that the relief portion 160B is disposed so as to be spaced apart from the first opening 121a. The distance (for example, an average distance at arbitrary 10 locations)

between the relief portion 160B and the first opening 121*a* is not particularly limited, but may be 50 μm or more, for example.

(Extrusion Suppression Portion)

In place of the frame body fixing portion 150 and the relief portion 160A, 160B, or together with the frame body fixing portion 150 and the relief portion 160A, 160B, a protrusion may be formed at at least a part of the circumference of the first opening 121*a*. This protrusion is an extrusion suppression portion that forcibly suppresses the extrusion of the first opening 121*a* caused by the bonding portion 140 being deformed by an external pressure. With the extrusion suppression portion, it is possible to suppress extrusion of the bonding portion 140 from the first opening 121*a* even when the bonding portion 140 is deformed, or when the positional relationship between the substrate 110 and the frame body 120 is changed.

Figure 7A:
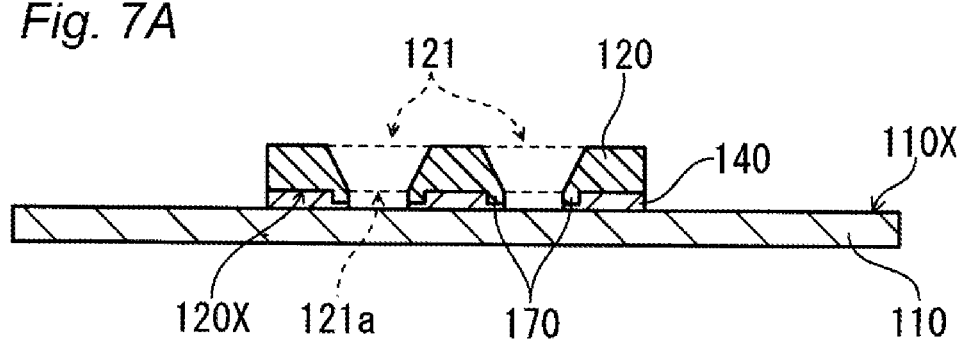
FIG. 7A is a cross-sectional view schematically showing a culture medium including an extrusion suppression portion.
Figure 7B:
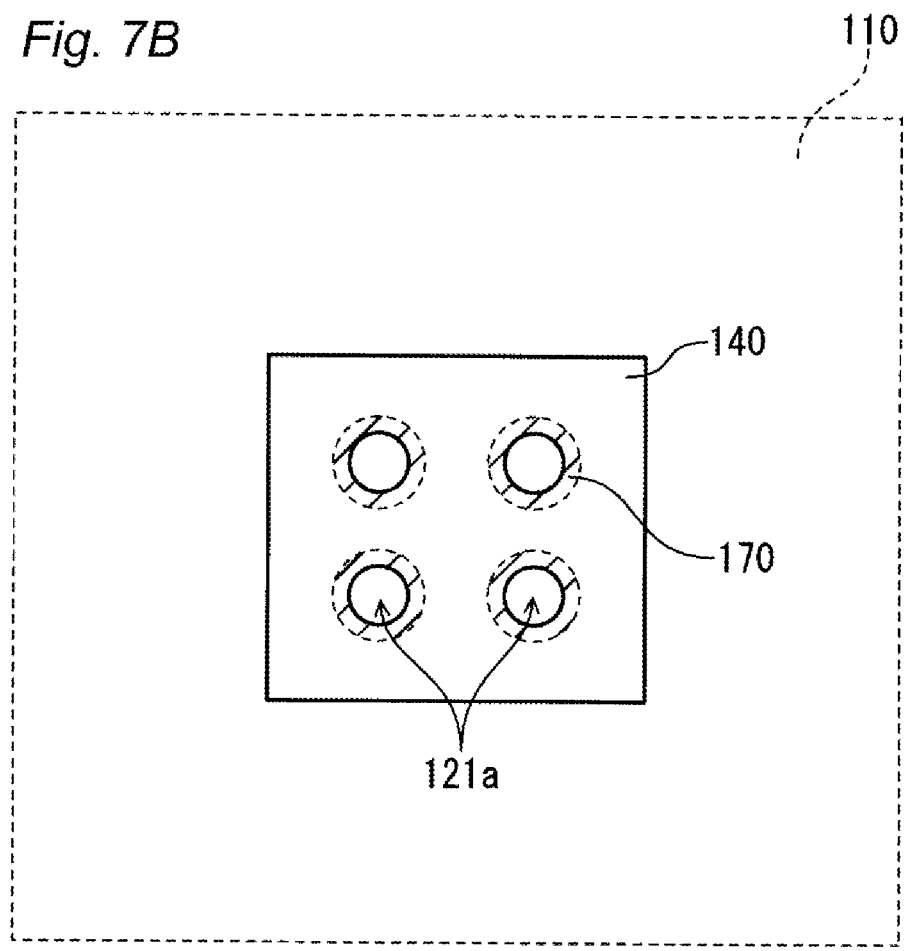
FIG. 7B is a plan view of the culture medium as viewed from the substrate side through the substrate.

The extrusion suppression portion will be described with reference to FIGS. 7A and 7B. Here, illustration of the group of fibers 130 is also omitted for the sake of convenience. FIG. 7A is a cross-sectional view schematically showing a culture medium 100 including an extrusion suppression portion 170. FIG. 7B is a plan view of the culture medium 100 shown in FIG. 7A, when viewed through the substrate 110 from the substrate 110 side. Note that in FIG. 7B, the extrusion suppression portion 170 is hatched for the sake of convenience.

The extrusion suppression portion 170 may be formed at at least a part of the circumference of the first opening 121*a*. In particular, since the extrusion of the bonding portion 140 can be easily suppressed, it is preferable that the extrusion suppression portion 170 is formed so as to surround the entire circumference of the first opening 121*a*. Such an extrusion suppression portion 170 may be a projection that may be formed together with the through hole 121 at the time of forming the through hole 121 by performing punching on the frame body 120.

The size of the extrusion suppression portion 170 is not particularly limited, and may be appropriately set according to the thickness and the like of the bonding portion 140. In particular, since the extrusion of the bonding portion 140 can be easily suppressed, the ratio of the height (length in the direction of the normal of the first surface 120X) of the extrusion suppression portion 170 to the thickness (length in the direction of the normal of the first surface 120X) of the bonding portion 140, when a cross-section of the culture medium 100 is viewed, is preferably 20 to 70%.

[Method for Producing Culture Medium]

In the present embodiment, in order to produce a culture medium 100 including a group of fibers 130 having high alignment performance, the fibers 131 are wound by a winding rotational body while being spun. Accordingly, the group of fibers 130 formed on the circumferential surface of the winding rotational body has high alignment performance in one direction. Furthermore, in a state in which the alignment of the fibers 131 in one direction is maintained, the group of fibers 130 is transferred onto the first surface 120X of the frame body 120. Thereafter, the frame body 120 including the group of fibers 130 is mounted onto the substrate 110 such that first surface 120X is opposed thereto. Consequently, the group of fibers 130 is disposed between the substrate 110 and the frame body 120, while maintaining the high alignment performance achieved when being wound by the winding rotational body.

The mounting surface 110X of the substrate 110 has an area sufficiently larger than the area of the frame body 120 for convenience of electric wiring. On the other hand, the group of fibers 130 may be disposed so as to be exposed from the first openings formed by plural through holes 121 formed in the frame body 120. Accordingly, by transferring the group of fibers 130 onto the frame body 120, rather than the substrate 110, the group of fibers 130 can be disposed only on the necessary portion without performing precise positioning or the like, so that the productivity is improved.

Figure 8A:
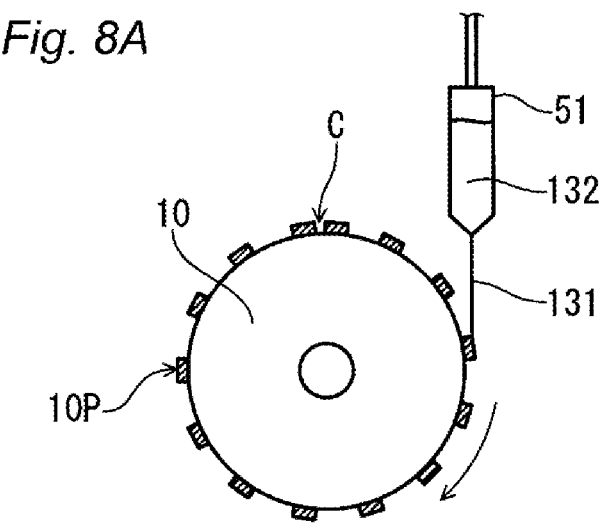
FIGS. 8A to 8C are side views schematically showing a winding rotational body, a frame body, and a substrate in steps for producing a culture medium.
Figure 8B:
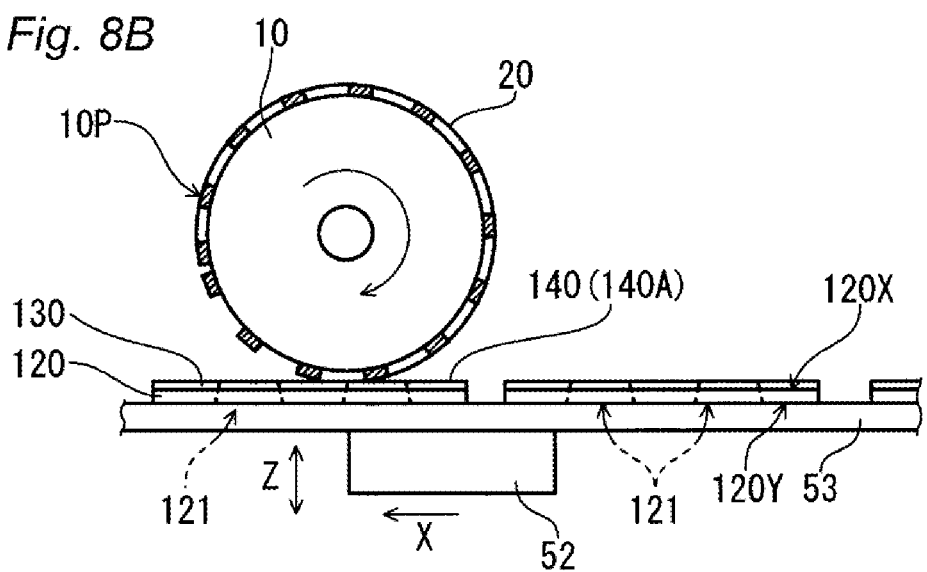
Figure 8C:
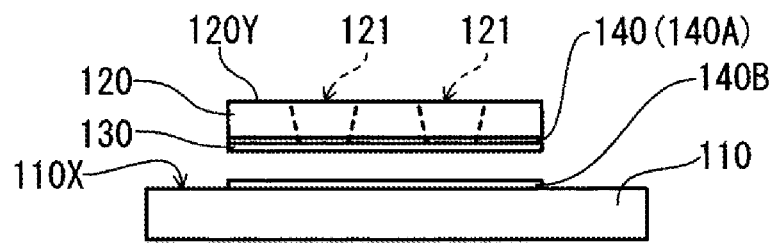

In the following, a production method of the present embodiment will be described with reference to the drawings. FIGS. 8A to 8C are side views schematically showing the winding rotational body 10, the frame body 120, and the substrate 110 etc., in steps of the present embodiment.

A method for producing a culture medium according to the present embodiment includes: for example, a preparation step of preparing a frame body 120 including a first surface 120X, a second surface 120Y opposite therefrom, and one or more through holes 121 extending from the first surface 120X through the second surface 120Y and a substrate 110 including a mounting surface 110X for mounting the frame body 120 thereon, the frame body 120 including a bonding portion 140 on at least one of a part of the first surface 120X and a part of the mounting surface 110X of the substrate 110; a deposition step of spinning a starting material liquid of fibers 131 from a nozzle 51 to generate the fibers 131, and depositing the fibers 131 so as to circumvent a circumferential surface of a winding rotational body 10, to form a group of fibers 130; a transfer step of transferring the group of fibers 130 onto the first surface 120X of the frame body 120, while rotating the winding rotational body 10; and a mounting step of mounting the frame body 120 having the group of fibers 130 transferred thereon to the substrate 110 such that the first surface 120X is opposed to the frame body 120.

The above-described production method may further include a frame body fixation step of fixing the frame body 120 to the substrate 110. By fixing the frame body 120 to the substrate 110, the deformation of the bonding portion 140 is suppressed. As a result, the initial tension and alignment of the fibers 131 can be easily maintained.

The production method of the present embodiment is performed by an apparatus including: for example, a bonding portion forming part that forms a bonding portion on at least one of a part of a first surface 120X of a frame body 120 and a part of a mounting surface 110X of a substrate 110; a depositing part that spins a starting material liquid of fibers 131 from a nozzle so as to generate fibers 131, and deposit the fibers 131 so as to circumvent the circumferential surface of a winding rotational body 10, to form a group of fibers 130; a transfer part that transfers the group of fibers 130 onto the first surface 120X of the frame body 120 via the bonding portion 140, while rotating the winding rotational body 10; and a mounting part that mounts, to the substrate 110, the frame body 120 having the group of fibers 130 transferred thereon such that the first surface 120X is opposed thereto. In the case where the frame body fixing portion 150 is disposed, the above-described apparatus may further include a curable resin application portion that applies a curable resin to a predetermined position of the frame body 120.

(1) Preparation Step

A substrate 110 including: a frame body 120 including a first surface 120X, a second surface 120Y opposite therefrom, and one or more through holes 121 extending from the first surface 120X through the second surface 120Y; and a mounting surface 110X for mounting the frame body 120 thereon is prepared.

A bonding portion 140 is formed on at least one of the first surface 120X and the mounting surface 110X. The bonding portion 140 is formed, for example, by printing or using a dispenser or the like, at a part other than a portion opposed to the first openings 121a, or the entire surface of the first surface 110X or the mounting surface 120X. Since the transfer of the group of fibers 130 onto the frame body 120 can be reliably performed, it is preferable that the bonding portion 140 is formed on at least the first surface 120X.

(2) Deposition Step (FIG. 8A)

Fibers 131 are generated from a starting material liquid 132, and are deposited while causing the fibers 131 to circumvent the circumferential surface of a winding rotational body 10 once or more. Consequently, a group of fibers 130 in which the fibers 131 are oriented in one direction is formed on the circumferential surface of the winding rotational body 10.

The method (spinning method) for generating the fibers 131 from the starting material liquid 132 is not particularly limited, and may be appropriately selected according to the type or the like of the fibers 131 to be generated. Examples of the spinning method include solution spinning, melt spinning, and electrospinning.

The fibers 131 are deposited along the circumferential surface of the winding rotational body 10, and may overlap each other in the direction of the normal of the circumferential surface. This overlap in the direction of the normal of fibers is often observed especially when fibers are generated by electrospinning. The fibers 131 that are deposited earlier tend to be moved by a stimulus from the fibers 131 that are deposited later, and tend to undergo orientation disorder. As will be described later, when the winding rotational body 10 includes protrusions 10P, the fibers 131 that are deposited earlier may be loosened between the protrusions 10P, thus undergoing orientation disorder. According to the present embodiment, after transferring the group of fibers 130 deposited on the winding rotational body 10 onto the frame body 120, the frame body 120 is further mounted onto the substrate 110 such that the group of fibers 130 is opposed thereto. Accordingly, in the resulting culture medium 100, the fibers 131 that are deposited later are disposed on the second surface 120Y side of the frame body 120. That is, the fibers 131 with less orientation disorder are disposed on the side that is more likely to be in contact with the nutrient solution. Accordingly, the stress to a biological tissue or a microorganism is reduced, thus further promoting the growth thereof.

Solution spinning is a method that uses, as the starting material liquid 132, a solution obtained by dissolving a starting material of the fibers 131 in a solvent. Solution spinning using a solvent includes the so-called wet spinning and dry spinning. In wet spinning, the starting material liquid 132 is spun into a solidification liquid, to form fibers 131 by chemical reaction between the starting material of the fibers 131 and the solidification liquid, or by substitution between the solvent and the solidification liquid. In dry spinning, the starting material liquid 132 is spun into the air, and thereafter the solvent is removed by heating or the like, thereby to form fibers 131. In particular, dry spinning is preferable because the fibers 131 can be easily deposited in a state of being aligned in one direction.

Melt spinning is a method that uses, as the starting material liquid 132, a melt obtained by melting a starting material of the fibers 131 by heating. The resulting starting material liquid 132 is spun into the air, and thereafter cooled to be solidified in the form of fibers. In this case, usually, a solvent for dissolving the starting material of the fibers 131 is not used. Thus, melt spinning is preferable in that the operation for removing the solvent can be omitted.

Electrospinning is similar to solution spinning in that it uses, as the starting material liquid 132, a solution obtained by dissolving a starting material of the fibers 131 in a solvent. However, in electrospinning, the starting material liquid 132 is spun into the air while a high voltage is being applied thereto. The solvent contained in the starting material liquid 132 undergoes volatilization in the process of reaching the circumferential surface of the winding rotational body 10.

In electrospinning, in order to apply a high voltage to the starting material liquid 132, the starting material liquid 132 is positively or negatively charged. At this time, the winding rotational body 10 is grounded, or charged with a polarity opposite to that of the starting material liquid 132, and, thereby, the emission end of the starting material liquid 132 spun into the air is drawn to the winding rotational body 10, and adheres to the circumferential surface thereof. Then, the winding rotational body 10 is rotated while spinning the starting material liquid 132. Thereby, as with solution spinning and melt spinning, the fibers 131 are deposited while circumventing the circumferential surface of the winding rotational body 10, and covers at least a part of the circumferential surface of the winding rotational body 10, thus forming a group of fibers 130 including the fibers 131 aligned in one direction.

(Starting Material Liquid)

The starting material liquid 132 used for solution spinning and electrospinning contains a starting material of the fibers 131 and a solvent. The starting material liquid 132 used for melt spinning contains a starting material of molten fibers 131.

The solvent is not particularly limited so long as it can dissolve the starting material of the fibers 131, and can be removed by volatilization or the like, and may be appropriately selected from water and an organic solvent according to the type of the starting material or the production conditions. As the solvent, it is preferable to use an aprotic polar organic solvent. Examples of such a solvent include amide (e.g., a non-cyclic or cyclic amide) such as N,N-dimethylformamide (DMF), N,N-dimethylacetamide (DMAc), and N-methyl-2-pyrrolidone (NMP); and sulfoxides such as dimethyl sulfoxide. These solvents may be used alone or in a combination of two or more.

The solid content concentration of the starting material liquid 132 can be adjusted according to the type of the solvent or the like, and is, for example, 5 to 50 mass %, or may be 10 to 30 mass %. The starting material liquid 132 may further contain an additive as needed.

(Winding Rotational Body)

Figure 9A:
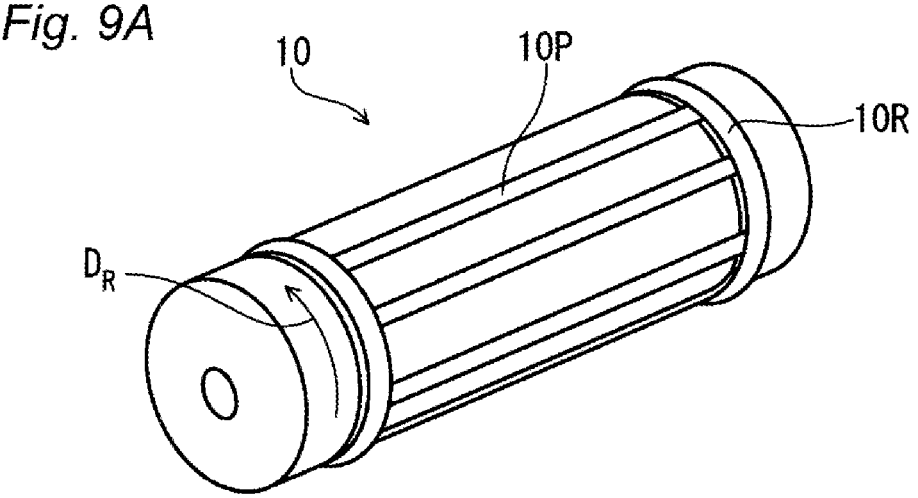
FIGS. 9A and 9B are a perspective view and a plan view showing an example of the winding rotational body according to the present invention.
Figure 9B:
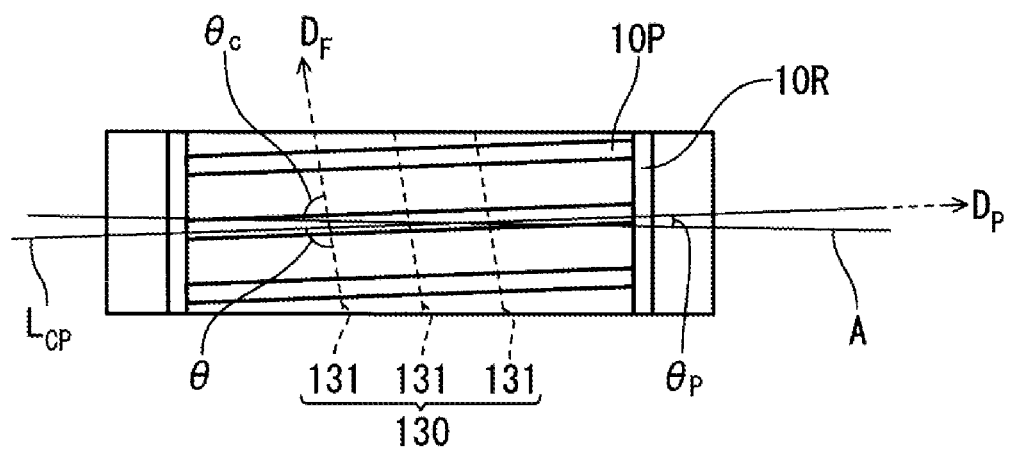

An example of the winding rotational body 10 is shown in FIGS. 9A and 9B. FIG. 9A is a perspective view of the winding rotational body 10, and FIG. 9B is a plan view thereof. In FIG. 9B, a part of the group of fibers 130 that is deposited on the circumferential surface of the winding rotational body 10 is also shown. The configuration of the winding rotational body 10 (or a rotational base 11, which will be described later) is not particularly limited so long as it is rotatable, and may be in the form of a drum, or a belt that is suspended by plural rolls. In the latter case, at least one roll is rotationally driven to rotate the belt. Examples of the material of the winding rotational body 10 include metal materials, various resins, various rubbers, ceramics, and a combination thereof. When the winding rotational body 10 is a belt, the belt may be a metal belt, or may be a resin belt. When the fibers 131 are spun by electrospinning, it is preferable that the resin belt has conductivity. The outside shape of the winding rotational body 10 may be, for example, columnar or prismatic.

The fibers 131 are deposited on the circumferential surface of the winding rotational body 10 while being aligned in a direction (hereinafter referred to as "alignment direction $D_F$") that circumvents the circumferential surface of the winding rotational body 10. The alignment direction $D_F$ is, for example, a direction along the rotational direction of the winding rotational body 10 (i.e., a direction perpendicular to the rotational axis of the winding rotational body 10). The angle $\theta_F$ (where $\theta_F \leq 90°$) formed between the alignment direction $D_F$ and the rotational axis may be, for example, 60° or more and 90° or less. Note that the alignment direction $D_F$ is the longitudinal direction of the fibers 131, when the fibers 131 are viewed from the direction of the normal of the circumferential surface of the winding rotational body 10. The longitudinal direction of the fibers 131 may be obtained by determining an approximation line for the fibers 131, as viewed from the direction of the normal of the circumferential surface of the winding rotational body 10. The angle $\theta_F$ is an average value of angles formed between the alignment directions $D_F$ of plural fibers 131 and the rotational axis. The alignment direction $D_F$ of the fibers 131 that are deposited on the winding rotational body 10 may be different from each other within the above-described range.

Plural strip-shaped protrusions 10P extending in a direction along the rotational axis of the winding rotational body 10 may be disposed on the circumferential surface of the winding rotational body 10. Accordingly, an aggregate (group of fibers 130) of the fibers 131 aligned so as to circumvent the circumferential surface of the winding rotational body 10 can be easily detached from the winding rotational body 10. As a result, the group of fibers 130 can be easily transferred onto the frame body 120, while maintaining the alignment of the fibers 131. Ends of the protrusions 10P may be joined by a rib 10R extending in a direction intersecting the rotational axis.

The extension direction $D_P$ of the protrusions 10P is not limited to be parallel to a rotational axis A, and the angle $\theta_P$ (where $\theta_P < 90°$) formed between the extension direction $D_P$ and the rotational axis A is, for example, 0° or more and 30° or less. In particular, in terms of the detachability of the group of fibers 130, the angle $\theta_P$ is preferably 0° or more and 20° or less.

The extension direction $D_P$ is a direction intersecting the alignment direction $D_F$ of the fibers 131. The angle $\theta$ (where $\theta_F \leq 90°$) formed between the extension direction $D_P$ and the alignment direction $D_F$ is, for example, 60° or more and 90° or less. Note that the extension direction $D_P$ is a direction of extension of a center line $L_{CP}$ of the protrusion 10P in the longitudinal direction, when the protrusions 10P are viewed from the direction of the normal of the circumferential surface of the winding rotational body 10. When the center line $L_{CP}$ includes a curve, the extension direction $D_P$ is a direction of extension of the center line of the smallest rectangle surrounding the center line $L_{CP}$.

The shape of the protrusion 10P is not particularly limited so long as it is a strip shape. The strip shape is a shape in which the length of the protrusion 10P in the extension direction is longer than the length in a direction perpendicular to the extension direction. Examples of the shape of the protrusion 10P as viewed from the direction of the normal of the circumferential surface of the winding rotational body 10 include a rectangular shape and a trapezoidal shape.

The number of the protrusions 10P is not particularly limited, so long as it is two or more. In particular, in terms of the detachability of the group of fibers 130, three or more protrusions 10P are disposed on the circumferential surface of the winding rotational body 10, preferably 10 or more protrusions 10P are disposed. From a similar viewpoint, it is preferable that the protrusions 10P are equidistantly disposed. Note that as will be described later, when the group of fibers 130 is cut while being wound around the winding rotational body 10 prior to a transfer step of the group of fibers 130 to the frame body 120 (see FIG. 8B), the group of fibers 130 is cut between the protrusions 10P such that at least a part of the cut group of fibers 130 is in contact with the protrusion 10P. Consequently, the alignment of the fibers 131 can be easily maintained. In this case, the interval between the protrusions 10P at a predetermined cut location C (see FIG. 8A) is preferably smaller than the intervals between the protrusions 10P at the other portions.

The length (width) of the protrusion 10P in the lateral direction is not particularly limited. In particular, from the viewpoint of the detachability of the group of fibers 130, it is preferable that the width of the protrusions 10P is determined such that a total area of all protrusions 10P that come into contact with the circumferential surface of the winding rotational body 10 is preferably 10% or more and 80% or less, particularly preferable 30% or more and 70% or less, of the surface area of the circumferential surface of the winding rotational body 10. The length of the protrusion 10P in the extension direction $D_P$ is also not particularly limited. In particular, it is preferable that the protrusions 10P extend on the circumferential surface of the winding rotational body 10 at least over a region in which the fibers 131 can be deposited.

The height of the protrusions 10P is not particularly limited. In particular, in order to suppress the loosening of the fibers 131 and easily maintain the alignment in one direction, it is preferable that the protrusions 10P is not excessively high. From the viewpoint of enhancing the detachability of the group of fibers 130 and suppressing the loosening of the fibers 131, the height of the protrusions 10P is preferably 100 to 5000 μm. The height of the protrusions 10P is an average value in the direction of the normal of the circumferential surface of the winding rotational body 10.

The material of the protrusion 10P is not particularly limited, and examples thereof include various resin materials. In particular, it is preferable that the protrusions 10P each include a silicone rubber layer at least at a portion thereof in contact with the fibers 131. The reason is that the detachability of the group of fibers 130 is further enhanced. On the other hand, the silicone rubber has a moderate viscosity, and thus suppresses the detachment of the group of fibers 130 from the circumferential surface of the winding rotational body 10 before the transfer step.

A silicone rubber is a thermosetting compound whose main chain is formed by a silicon-oxygen bond (siloxane bond). Examples of the silicone rubber include a methyl silicone rubber, a vinyl-methyl silicone rubber, a phenyl-methyl silicone rubber, a dimethyl silicone rubber, and a fluorosilicone rubber. Each of the protrusions 10P may entirely formed of the silicone rubber. Note that when the fibers 131 are generated by electrospinning, it is preferable that the protrusions 10P have conductivity.

Figure 10:
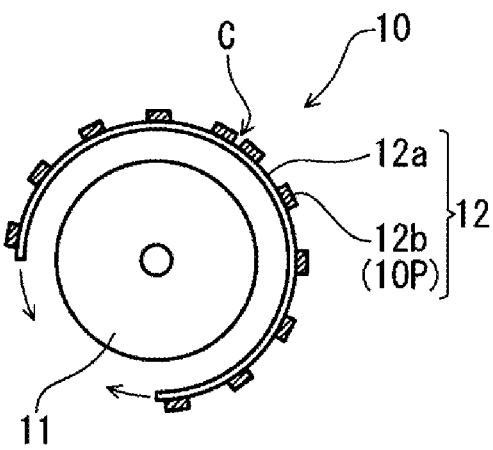
FIG. 10 is a side view showing another example of the winding rotational body according to the present invention.

From the viewpoint of handleability, it is preferable that the protrusions 10P are removably disposed on the winding rotational body 10. For example, as shown in FIG. 10, an uneven sheet 12 including a support sheet 12a and silicone rubbers 12b disposed in the form of strips on the surface of the support sheet 12a may be prepared, and the uneven sheet 12 may be wound around the circumference of a rotational base 11. In this case, the silicone rubbers 12b correspond to the protrusions 10P. This configuration facilitates the arrangement of the protrusions 10P, and also facilitates the replacement when the protrusions 10P are deteriorated.

The material of the support sheet 12a is not particularly limited, and examples thereof include polyesters such as polyethylene terephthalate and polyimides. When the fibers 131 are generated by electrospinning, it is preferable that the support sheet 12a also has conductivity. The thickness of the support sheet 12a is also not particularly limited, and may be appropriately set according to the material and the like of the support sheet 12a. Examples of the silicone rubber 12b include the above-listed compounds.

A heating step of heating at least one of the group of fibers 130 and the frame body 120 may be included after the deposition step and before the transfer step. By heating the group of fibers 130 before the transfer step, the group of fibers 130 is transferred in a softened state onto the frame body 120. This enhances the adhesion between the group of fibers 130 and the frame body 120. Further, by heating the frame body 120 before the transfer step, the heat is conducted to the group of fibers 130 after the transfer, to soften the group of fibers 130. This enhances the adhesion between the group of fibers 130 and the frame body 120. In particular, the method heating the frame body 120 is preferable in that the degradation of the fibers 131 can be suppressed.

The heating method is not particularly limited, but is preferably a non-contact method because the alignment of the fibers 131 can be maintained. Examples of a non-contact heating device include known heating devices such as a halogen lamp. The heating temperature may be appropriately set according to the softening point or the melting point of the fibers 131. The heating temperature is adjusted, for example, such that the temperature of the fibers 131 is 80 to 140° C.

(3) Transfer Step (FIG. 8B)

The group of fibers 130 is transferred onto the frame body 120, while rotating the winding rotational body 10. Prior to the transfer step, the group of fibers 130 may be cut at a predetermined cut portion C in a state in which it is wound around the winding rotational body 10. The predetermined cut portion C is set, for example, according to the shape and the size of the frame body 120 (or the first openings 121a). The group of fibers 130 is cut, for example, in a direction along the rotational axis of the winding rotational body 10. With the cut portion as the starting point, the group of fibers 130 is transferred onto the frame body 120.

The frame body 120 is transported while being placed, for example, on a stage 53 supported by an XZ stage 52. The XZ stage 52 can transport the stage 53, or in other words, the frame body 120 placed on the stage 53, in a direction (X-axis direction) perpendicular to the rotational axis of the winding rotational body 10 and the up-down direction (Z-axis direction).

It is preferable that the transfer step is performed on plural frame bodies 120 collectively or successively because this further enhances the productivity. In this case, the frame bodies 120 may be disposed on the stage 53 along a Y-axis direction (direction along the rotational axis of the winding rotational body 10), or may be disposed along the X-axis direction. The transfer step may be performed on an aggregate of plural frame bodies 120 that are integrally formed. In this case, the aforementioned aggregate of the frame bodies 120 is separated into the individual frame bodies 120 after the transfer step and before the mounting step. With this method, the group of fibers 130 can be transferred onto the frame bodies 120 collectively, and the majority of the fibers 131 deposited on the winding rotational body 10 can be used to transfer the frame body 120, thus further enhancing the productivity.

(4) Mounting Step (FIG. 8C)

The frame body 120 having the group of fibers 130 transferred thereon is mounted on a substrate 110 such that a first surface 120X is opposed thereto.

At this time, a bonding portion 140 (or a first bonding portion 140A) and the group of fibers 130 are interposed between the frame body 120 and the substrate 110. A second bonding portion 140B may be disposed on the substrate 110, and the second bonding portion 140B may be further interposed between the frame body 120 and the substrate 110. Even when the transfer step is performed on the frame bodies 120 collectively or successively, one frame body 120 is mounted on one substrate 110.

(5) Frame Body Fixation Step

After the step of forming a bonding portion, or after the mounting step, a curable resin is applied to a predetermined position of the first surface 120 X and is cured, thereby to form a frame body fixing portion 150.

INDUSTRIAL APPLICABILITY

A culture medium obtained by the present invention includes fibers aligned in one direction, and therefore is useful especially as a culture medium for culturing a biological tissue or a microorganism having directionality in growth. Furthermore, with the method according to the present invention, a culture medium including a group of fibers including fibers aligned in one direction can be produced with good productivity.

REFERENCE SIGNS LIST

10. . . . Winding rotational body
10P. . . . Protrusion
10R. . . . Rib
11. . . . Rotational base
12. . . . Uneven sheet
12a . . . . Support sheet
12b . . . . Silicone rubber
51. . . . Nozzle
52. . . . XZ stage
53. . . . Stage
100. . . . Culture medium
110. . . . Substrate
110X. . . . Mounting surface
120. . . . Frame body
120X. . . . First surface
120Y. . . . Second surface
121. . . . Through hole
121a . . . . First opening
122. . . . Notch
130. . . . Group of fibers
131. . . . Fiber
132. . . . Starting material liquid
140. . . . bonding portion
140A. . . . First bonding portion
140B. . . . Second bonding portion
150. . . . Frame body fixing portion
160A, 160B. . . . Relief portion
170. . . . Extrusion suppression portion

What is claimed is:
1. A culture medium comprising:
a substrate;

a frame body that includes a first surface, a second surface opposite therefrom, and one or more through holes extending from the first surface through the second surface, and that is mounted to the substrate such that the first surface is opposed thereto;
a plurality of aligned fibers interposed between the substrate and the first surface;
a bonding portion that bonds the substrate, the plurality of aligned fibers, and the frame body, and
a frame body fixing portion that fixes the frame body to the substrate,
wherein
at least a part of the plurality of aligned fibers is exposed from a first opening that is formed in the first surface by the through hole,
the bonding portion is opposed to the first surface,
at least a portion of the frame body fixing portion is in contact with an outer peripheral surface of the frame body, and
the frame body fixing portion is not in contact with a bottom surface of the frame body.

2. The culture medium in accordance with claim 1, wherein
the bonding portion includes a pressure-sensitive adhesive.

3. The culture medium in accordance with claim 1, wherein
the frame body fixing portion includes a cured product of a curable resin.

4. The culture medium in accordance with claim 2, further comprising a recess capable of housing therein at least a part of the adhesive is formed on the first surface at a position corresponding to a part of the bonding portion.

5. The culture medium in accordance with claim 2, further comprising a space in which at least a part of the adhesive can move is formed between the substrate and the frame body at a position corresponding to the first surface.

6. The culture medium in accordance with claim 2, further comprising a protrusion that suppresses extrusion of the adhesive into the first opening is formed on at least a part of a circumference of the first opening.

7. The culture medium in accordance with claim 1, wherein
an entire portion of the frame body fixing portion is disposed outside of the bonding portion.

* * * * *